(12) United States Patent
Shimada et al.

(10) Patent No.: US 6,710,222 B2
(45) Date of Patent: Mar. 23, 2004

(54) DISPOSABLE UNDERGARMENT

(75) Inventors: Takaaki Shimada, Kagawa-ken (JP); Kenji Nakamura, Kagawa-ken (JP); Seiji Suzuki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 3 days.

(21) Appl. No.: 09/880,661

(22) Filed: Jun. 13, 2001

(65) Prior Publication Data

US 2001/0056269 A1 Dec. 27, 2001

(30) Foreign Application Priority Data

Jun. 27, 2000 (JP) ......................................... 2000-192301

(51) Int. Cl.$^7$ ................................................. A61F 13/15
(52) U.S. Cl. ........................ 604/366; 604/365; 604/372
(58) Field of Search ................................. 604/365, 366, 604/367, 368, 372; 428/198, 297.4, 298.1, 299.7; 267/495, 322, 494

(56) References Cited

U.S. PATENT DOCUMENTS

| | | | |
|---|---|---|---|
| 4,886,697 A | * 12/1989 | Perdelwitz, Jr et al. | 428/192 |
| 5,300,054 A | * 4/1994 | Feist et al. | 604/378 |
| 5,318,552 A | * 6/1994 | Shiba et al. | 604/366 |
| 5,352,480 A | * 10/1994 | Hansen et al. | 427/202 |
| 5,411,497 A | * 5/1995 | Tanzer et al. | 604/368 |
| 5,486,167 A | * 1/1996 | Dragoo et al. | 604/384 |
| 5,516,569 A | * 5/1996 | Veith et al. | 428/68 |
| 5,558,655 A | * 9/1996 | Jezzi et al. | 604/378 |
| 5,589,256 A | * 12/1996 | Hansen et al. | 428/283 |
| 5,591,149 A | * 1/1997 | Cree et al. | 604/378 |
| 5,762,642 A | * 6/1998 | Coles et al. | 604/378 |
| 5,821,179 A | * 10/1998 | Masaki et al. | 442/375 |

FOREIGN PATENT DOCUMENTS

JP          8-196559          8/1996

* cited by examiner

*Primary Examiner*—Weilun Lo
*Assistant Examiner*—Jacqueline F Stephens
(74) *Attorney, Agent, or Firm*—Butzel Long

(57) ABSTRACT

A disposable undergarment having a liquid-absorbent panel that includes a body fluid absorbing/holding layer formed with a plurality of depressions each extending in the thickness direction thereof and a nonwoven fabric layer placed upon upper surface of the absorbing/holding layer. Heat-sealable fibers contained in the absorbing/holding layer are heat-sealed with the nonwoven fabric layer over contacting surfaces of these absorbing/holding layer and the nonwoven fabric layer. Furthermore, the nonwoven fabric layer is partially engaged in the depressions of the absorbing/holding layer so that the heat-sealable synthetic fibers contained in the absorbing/holding layer are heat-sealed with the nonwoven fabric layer also over contacting surfaces of these two layers in the respective depressions.

4 Claims, 3 Drawing Sheets

DISPOSABLE UNDERGARMENT

BACKGROUND OF THE INVENTION

This invention relates to a disposable undergarment and more particularly to such undergarment including a disposable diaper, a training pant and an incontinent pant.

Japanese Patent Application Publication No. 1996-196559A describes the disposable diaper comprising a liquid-pervious topsheet, a liquid-impervious backsheet and a liquid-absorbent panel. The panel consisting of a body fluid absorbing/holding layer comprising fluff pulp in a content less than 70% by weight and high absorption polymer particles in a content of 30% by weight or higher and a fibrous assembly layer placed upon the top surface of the absorbing/holding layer. In the diaper of prior art, the absorbing/holding layer and the fibrous assembly layer are integrally covered with tissue paper so that substantially entire contacting surfaces of these absorbing/holding layer, fibrous assembly layer and tissue paper are intermittently bonded together by means of hot melt adhesive. This diaper of prior art is claimed to ensure that these absorbing/holding layer, fibrous assembly layer and tissue paper can be kept in close contact one with another even if the diaper is distorted.

The fibrous assembly layer certainly has a function to prevent the absorbing/holding layer from getting out of its initial shape. However, the absorbing/holding layer and the fibrous assembly layer are bonded to each other merely over their contacting surfaces, so that the regions of these layers except the contacting surfaces are apt to get out of their shapes. If the non-bonded region of the absorbing/holding layer gets out of the shape as the panel is deformed due to movement of a wearer, it is apprehended that the absorbing/holding layer might be separated from the fibrous assembly layer and a rapid absorption of body fluids in the panel might be obstructed.

SUMMARY OF THE INVENTION

It is an object of this invention to provide a disposable undergarment designed so as to prevent the body fluid absorbing/holding layer from getting out of its initial shape and thereby to ensure desirably rapid absorption of body fluids in the panel.

According to this invention, there is provided a disposable undergarment comprising a liquid-pervious topsheet, a liquid-impervious backsheet and a liquid-absorbent panel disposed between the top- and backsheets, wherein the panel comprises a body fluid absorbing/holding layer formed with a mixture of fluff pulp, high absorption polymer particles and heat-sealable synthetic resin fibers and a nonwoven fabric layer made of heat-sealable synthetic resin fibers placed upon at least one of upper and lower surfaces of the body fluid absorbing/holding layer and wherein the absorbing/holding layer and the nonwoven fabric layer are integrally covered with and bonded to a water-pervious sheet.

According to this invention is the heat-sealable synthetic resin fibers contained in the absorbing/holding layer are heat-sealed with the nonwoven fabric layer over contacting surfaces of the absorbing/holding layer and the nonwoven fabric layer.

According to one embodiment of this invention, the absorbing/holding layer is formed on its surface opposed to the nonwoven fabric layer with a plurality of depressions each extending in a thickness direction thereof and the nonwoven fabric layer is partially engaged with the depressions so that the heat-sealable synthetic resin fibers contained in the absorbing/holding layer are heat-sealed with the nonwoven fabric layer over contacting surfaces of the absorbing/holding layer and the nonwoven fabric layer in the depressions.

According to another embodiment of this invention, the nonwoven fabric layer has a tear strength higher than that of the absorbing/holding layer.

According to still another embodiment of this invention, the absorbing/holding layer comprising the fluff pulp in a content of 15–67% by weight, the high absorption polymer grains in a content of 30–70% by weight and the heat-sealable synthetic resin fibers in a content of 3–15% by weight.

According to further another embodiment of this invention, the heat-sealable synthetic resin fibers contained in the absorbing/holding layer as well as the heat-sealable synthetic resin fibers forming the nonwoven fabric layer have been previously treated to have hydrophilicity.

DETAILED DESCRIPTION OF THE PREFERRED EMBODIMENTS

Details of the disposable wearing article according to this invention will be more fully understood from the description given hereunder with reference to the accompanying drawings.

Figure 1:
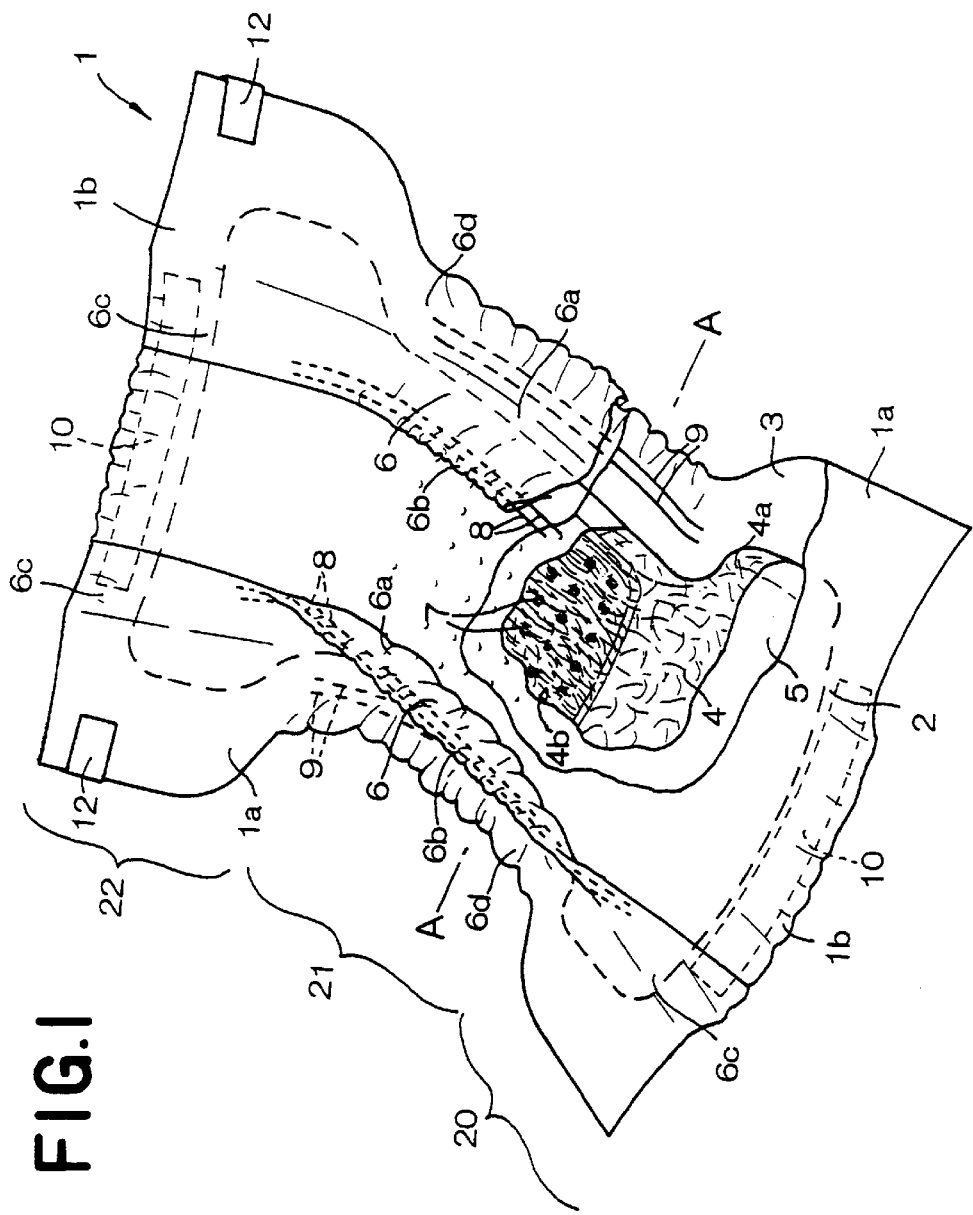
FIG. 1 is a perspective view showing a disposable diaper from its front waist region as partially broken away.
Figure 2:
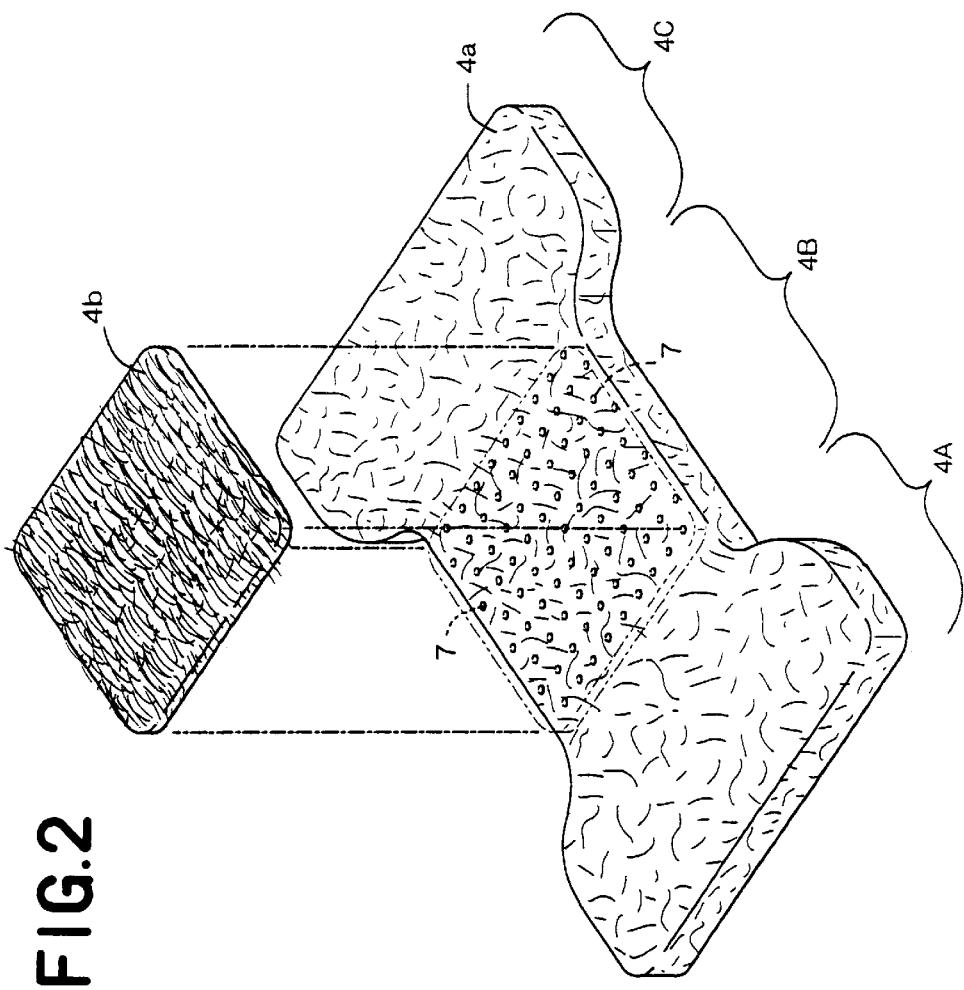
FIG. 2 is a developed plan view showing the diaper prior to folding the diaper into a pant-type.
Figure 3:
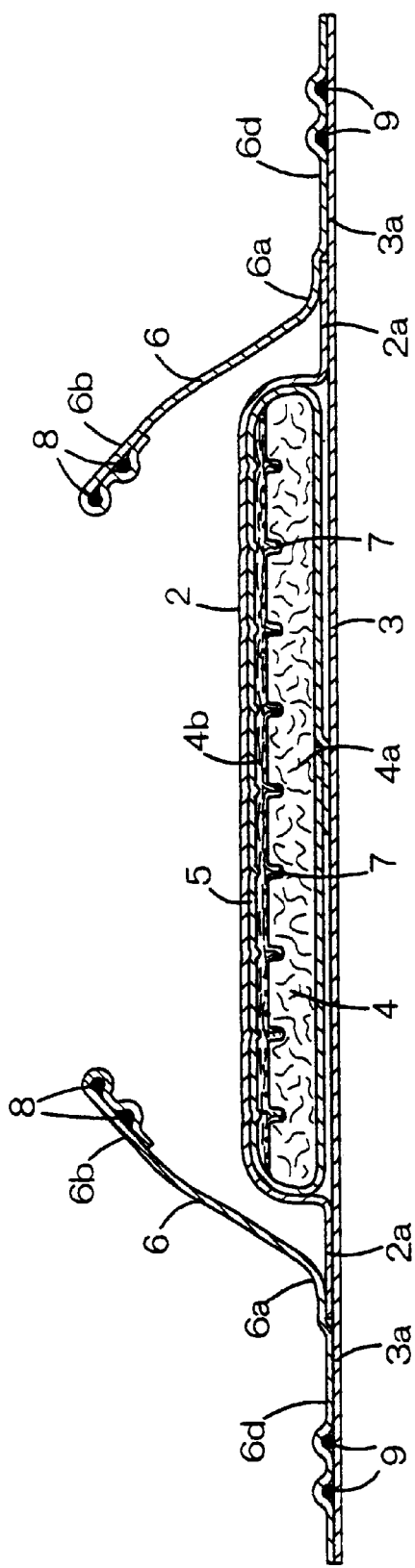
FIG. 3 is a sectional view taken along a line A—A in FIG. 2.

FIG. 1 is a perspective view showing a disposable diaper 1 as partially broken away, FIG. 2 is an exploded perspective view showing a liquid absorbent panel 4 as a body fluid absorbing/holding layer 4a being separated from a nonwoven fabric layer 4b and FIG. 3 is a sectional view taken along a line A—A in FIG. 1. Referring to FIG. 2, chain lines indicate the nonwoven fabric layer 4b placed upon the body fluid absorbing/holding layer 4a. The diaper 1 basically comprises a liquid-pervious topsheet 2, a liquid-impervious backsheet 3 and a liquid-absorbent panel 4 disposed between the top- and backsheets 2, 3.

As will be seen in FIG. 1, the diaper 1 is composed, in its longitudinal direction, a front waist region 20, a rear waist region 22 and a crotch region 21 extending between the front and rear waist regions 20, 22. The diaper 1 has transversely opposite side edge portions 1a extending in parallel to each other in the longitudinal direction and curving, in the crotch region 21, transversely inward so as to describe circular arcs and longitudinally opposite end portions 1b extending in parallel to each other in the transverse direction. The transversely opposite side edge portions 1a are provided with leak-proof cuffs 6 extending in the longitudinal direction.

The panel 4 comprises the body fluid absorbing and holding layer 4a and the nonwoven fabric layer 4b placed upon the upper surface of the absorbing/holding layer 4a. The panel 4 has its entire surface covered with a water-pervious sheet such as tissue paper 5 and is bonded to inner surface of at least one of the top- and backsheets 2, 3 with the tissue paper 5 interposed therebetween. The panel 4 and the tissue paper 5 are bonded to each other by means of dot-like adhesive (not shown) applied on at least one of the panel 4 and tissue paper 5.

The absorbing/holding layer 4a is formed with a mixture of fluff pulp, high absorption polymer particles and heat-sealable synthetic resin fiber compressed to a desired thickness. The absorbing/holding layer 4a is hourglass-shaped and has a front region 4A lying in the front waist region 20 of the diaper 1, a rear region 4C lying in the rear waist region 22 of the diaper 1 and a middle region 4B lying in the crotch region 21 of the diaper 1. The absorbing/holding layer 4a is formed on its upper surface with a plurality of depressions 7 in a thickness direction of the absorbing/holding layer 4a. Within the absorbing/holding layer 4a, the individual heat-sealable fibers are mechanically intertwined or fused together at their intersecting points.

The nonwoven fabric layer 4b is formed with the heat-sealable synthetic resin fiber and positioned on the middle region 4B of the absorbing/holding layer 4a. The nonwoven fabric layer 4b has a tear strength higher than that of the absorbing/holding layer 4a. The nonwoven fabric layer 4b preferably has a tear strength of 50 g/25 mm or higher as measured according to JIS:L1096.

The individual heat-sealable fibers of the absorbing/holding layer 4a are heat-sealed with the nonwoven fabric layer 4b along contacting surfaces of the absorbing/holding layer 4a and the nonwoven fabric layer 4b placed upon each other. In addition, the nonwoven fabric layer 4b is partially engaged into the depressions 7 of the absorbing/holding layer 4a so that the individual heat-sealable synthetic resin fibers of the absorbing/holding layer 4a are heat-sealed with the nonwoven fabric layer 4b also along their contacting surfaces within the respective depressions 7.

In the panel 4, the heat-sealable fibers entangled with the individual heat sealable fibers within the absorbing/holding layer 4a serve to improve a shape-stability of the absorbing/holding layer 4a. The absorbing/holding layer 4a and the nonwoven fabric layer 4b are heated with each other also in the respective depressions 7 of the absorbent/holding layer 4a and thus the number of fusion spots of these layers 4a, 4b correspondingly increases with a result that these two layers 4a, 4b are further firmly bonded together.

The individual heat-sealable fibers of the absorbing/holding layer 4a cooperate with component fibers of the nonwoven fabric layer 4b to ensure these two layers 4a, 4b to be easily and reliably sealed with one another. In view thereof, it is preferable that the component fibers of these two layers 4a, 4b have their melting points approximate to each other and are subjected to suitable treatment to make them hydrophilic so that the body fluids discharged on the diaper may smoothly spread.

The nonwoven fabric layer 4b preferably has a basis weight of 10–100 g/m$^2$, more preferably of 10–30 g/m$^2$. The basis weight less than 10 g/m$^2$ would cause the nonwoven fabric layer 4b to be broken due to its deformation and consequently the absorbing/holding layer 4a may get out its shape due to as the nonwoven fabric layer 4b is broken. The basis weight exceeding 100 g/m$^2$, on the other hand, would deteriorate a flexibility of the nonwoven fabric layer 4b and correspondingly deteriorate a feeling to wear the diaper 1.

In the absorbing /holding layer 4a, the fluff pulp has a content of 15–67% by weight, the high absorption polymer grains have a content of 30–70% by weight and the heat-sealable fiber has a content of 3–15% by weight. The content of the heat-sealable fiber less than 3% by weight would lead to insufficient heat-sealing between the absorbing/holding layer 4a and the nonwoven fabric layer 4b and, in consequence, the absorbing/holding layer 4a and the nonwoven fabric layer 4b may be separated from each other due to deformation of the panel 4. The content of the heat-sealable fiber exceeding 15% by weight would deteriorate the flexibility of the absorbing/holding layer 4a and correspondingly deteriorate a feeling to wear the diaper 1.

Each of the cuffs 6 has a fixed side edge portion 6a fixed to the topsheet 2, a free side edge portion 6b opposed to the fixed side edge portion 6a and extending in the longitudinal direction of the diaper 1, longitudinally opposite end portions 6c collapsed inward in the transverse direction of the diaper 1 and fixed to the topsheet 2 in such state, and an outer side edge portion 6d extending outward from the fixed side edge portion 6a in the transverse direction of the diaper 1. A longitudinally extending elastic member 8 is bonded under tension to the free side edge portion 6b of the cuff 6 so as to be covered with a portion of the free side edge portion 6b. The cuff 6 has its free side edge portion 6b is normally biased by the elastic member 8 to rise on the topsheet 2.

The diaper 1 is provided along the transversely opposite side edge portions 1a with a plurality of leg-opening associated elastic members 9 extending in the longitudinal direction of the diaper 1 and bonded under tension to the diaper 1. These elastic members 9 are disposed between the transversely opposite side edge portions 3a of the backsheet 3 and the outer side edge portions 6d of the respective cuffs 6 and fixed to inner surface of the backsheet 3 and/or the cuffs 6.

The diaper 1 is provided along the longitudinally opposite end portions 1b with waist-opening associated elastic members 10 extending in the transverse direction of the diaper 1 and bonded under tension to the diaper 1. Portions of the waist-opening associated elastic members 10 lying on the transversely opposite side edge portions 1a of the diaper 1 are disposed between the transversely opposite side edge portions 3a of the backsheet 3 and the outer side edge portions 6d of the respective cuffs 6 and fixed to inner surface of the backsheet 3 and/or the cuffs 6. The remaining portions of these elastic members 10 are disposed between the top- and backsheets 2, 3 and fixed to inner surface of the topsheet 2 and/or the backsheet 3.

Referring to FIG. 1, a plurality of gathers are formed along the transversely opposite side edge portions 1a as well as the longitudinally opposite end portions 1b of the diaper 1 and the free side edge portions 6b of the respective cuffs 6 as the elastic members 8, 9, 10 contract, respectively. Thereupon, the free side edge portions 6b of the respective cuffs 6 rise upward from the inner side of diaper 1 as viewed in FIG. 1.

The rear waist region 22 is provided on the side edge portions 1a with tape fasteners 12 extending inward transversely of the diaper 1. The front waist region 20 is provided on the outer surface of the backsheet 3 with a target tape strip (not shown) on which the tape fasteners 12 are destined to be anchored.

The tape fasteners 12 have proximal end portions thereof disposed between the top- and backsheets 2, 3 and fixed to inner surfaces of these sheets 2, 3 by means of adhesive (not shown). The tape fasteners 12 have free end portions coated on inner surfaces thereof with pressure-sensitive adhesive (not shown) by means of which the free end portions of the tape fasteners 12 are peelably bonded to the topsheet 2.

To wear the diaper 1, the free end portions of the tape fasteners 12 may be anchored on the outer surface of the target tape strip by means of the pressure-sensitive adhesive so as to form a waist-opening (not shown) and a pair of leg-openings (not shown).

In the vicinity of the transversely opposite side edge portions 1a of the diaper 1, transversely opposite side edge portions 2a of the topsheet 2 transversely extend outward slightly beyond opposite side edges of the panel 4 and transversely opposite side edge portions 3a of the backsheet 3 as well as the outer side portions 6d of the cuffs 6 transversely extend further outward beyond the side edge portions 3a of the topsheet 3. The side edge portions 2a of the topsheet 2 are disposed between the side edge portions 3a of the backsheet 3 and the outer side portions 6d of the cuffs 6 and bonded to inner surface of the backsheet 3 and/or the cuffs 6. The side edge portions 3a of the backsheet 3 are put flat together with the outer side portions 6d of the cuffs 6 and the inner surfaces thereof opposed to each other are bonded together. Along the longitudinally opposite end portions 1b of the diaper 1, portions of the top- and backsheets 2, 3 longitudinally extending outward beyond longitudinally opposite ends of the panel 4 are put flat together and firmed bonded to each other.

The nonwoven fabric layer 4b may be placed on at least one of upper and lower surfaces of the absorbing/holding layer 4a so that the nonwoven fabric layer 4b may cover at least the middle region 4B of the absorbing/holding layer 4a including the front, rear and middle regions 4A, 4C, 4B.

The nonwoven fabric layer 4b may be formed from a nonwoven fabric selected from a group including those of spunlace-, needlepunch-, meltblown, thermalbond-, spunbond-, chemicalbond- and airthrough-types. The heat-sealable fiber as the component fiber of the absorbing/holding layer 4a as well as the component fiber of the nonwoven fabric layer 4b may be selected from a group including polyolefine-, polyester- and polyamide-based fibers, core-sheath-type conjugated fibers, eccentric core-sheath-type conjugated fibers or side-by-side-type conjugated fibers of polyethylene/polypropylene or polyester.

The topsheet 2 may be formed from a liquid-pervious sheet made of a nonwoven fabric or porous plastic film, preferably with a liquid-pervious hydrophilic sheet. The backsheet 3 may be formed from a hydrophobic nonwoven fabric or a liquid-impervious plastic film or a laminated sheet of a hydrophobic nonwoven fabric and a plastic film, preferably by a breathable but liquid-impervious sheet. For the backsheet 3, it is also possible to use a composite nonwoven fabric (SMS nonwoven fabric) consisting of a melt blown nonwoven fabric having a high water-resistance of which opposite sheet surfaces are sandwiched between sheet surfaces of two layers of a spun bond nonwoven fabric having high strength and flexibility.

Bonding between the top- and backsheets 2, 3, bonding between these top- and backsheets 2, 3 and the tissue paper 5 and attachment of the elastic members 8, 9, 10 may be carried out using suitable adhesive such as hot melt adhesive and pressure-sensitive adhesive or thermal sealing means such as heat-sealing and sonic sealing. The hot melt is preferably adhesive.

This invention is not limited to a disposable diaper but applicable also to training pants, incontinent pants and the like. This invention can be implemented not only in the form of an open-type diaper as having been illustrated and described but also in the form of a pants-type diaper.

The disposable undergarment according to this invention ensures that the absorbing/holding layer not easily gets out of its initial shape and the body fluids are rapidly absorbed in the panel. This is because the heat-sealable fibers of the absorbing/holding layer provide a shape-stability of this absorbing/holding layer and the heat-sealable fibers of the absorbing/holding layer are heat-sealed with the nonwoven fabric layer over the contacting surfaces of these two layers.

In the panel, the body fluid absorbing/holding layer is formed on its surface opposed to the nonwoven fabric layer with a plurality of depressions each extending in the thickness direction thereof. The nonwoven fabric layer is partially engaged in the depressions so that the heat-sealable fibers of the absorbing/holding layer are heat-sealed with the nonwoven fabric layer also in the depressions. In this way, the number of spots at which the absorbing/holding layer and the nonwoven fabric layer are heat-sealed with each other correspondingly increases. Consequently, these two layers are further firmly connected to each other and the absorbing/holding layer is further reliably protected against getting out of its initial shape.

What is claimed is:

1. A disposable undergarment comprising:

a liquid-pervious top sheet;

a liquid-impervious backsheet; and a liquid-absorbent panel disposed between said topsheet and said backsheet, said liquid-absorbent panel comprising:

a body fluid absorbing/holding layer comprising a mixture of fluff pulp, high absorption polymer particles and heat-sealable resin fibers, said body fluid absorbing/holding layer including an upper and a lower surface and a plurality of depressions formed in at least one of the upper and the lower surface; and a nonwoven fabric layer comprising heat-sealable synthetic resin fibers, said nonwoven fabric layer being placed upon at least one of the upper and lower surface of said body fluid absorbing/holding layer which includes said plurality of depressions, and said absorbing/holding layer and said nonwoven fabric layer being integrally covered with and bonded to a water-pervious sheet, said heat-sealable synthetic resin fibers of said absorbing/holding layer being heat-sealed with said nonwoven fabric layer over contacting surfaces of said absorbing/holding layer and said nonwoven fabric layer and further beat-sealed within the plurality of depressions in the adjacent contacting surface of the body fluid absorbing/holding layer so as to substantially fill said plurality of depressions.

2. The disposable undergarment according to claim 1, wherein said nonwoven fabric layer has a tear strength that is higher than a tear strength of said absorbing/holding layer.

3. The disposable undergarment according to claim 1, wherein said absorbing/holding layer comprises about 15 to about 67% by weight if said fluff pulp, about 30 to about 70% by weight of said high absorption polymer particles, and about 3 to about 15% by weight of said heat-sealable synthetic resin fibers.

4. The disposable undergarment according to claim 1, wherein said heat-sealable synthetic resin fibers of said absorbing/holding layer as well as said heat-sealable synthetic resins fibers of said nonwoven layer are hydrophilic.

* * * * *